US008822540B2

(12) United States Patent
Brooks et al.

(10) Patent No.: US 8,822,540 B2
(45) Date of Patent: Sep. 2, 2014

(54) NITISINONE FOR TREATMENT OF OCULOCUTANEOUS/OCULAR ALBINISM AND FOR INCREASING PIGMENTATION

(75) Inventors: Brian P. Brooks, Kensington, MD (US); William A. Gahl, Kensington, MD (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 0 days.

(21) Appl. No.: 13/580,452

(22) PCT Filed: Feb. 25, 2011

(86) PCT No.: PCT/US2011/026260
§ 371 (c)(1),
(2), (4) Date: Sep. 6, 2012

(87) PCT Pub. No.: WO2011/106655
PCT Pub. Date: Sep. 1, 2011

(65) Prior Publication Data
US 2012/0322887 A1    Dec. 20, 2012

Related U.S. Application Data

(60) Provisional application No. 61/308,771, filed on Feb. 26, 2010.

(51) Int. Cl.
*A61K 31/13* (2006.01)
*A61K 31/135* (2006.01)

(52) U.S. Cl.
USPC ............ 514/612; 514/645; 514/646; 514/657

(58) Field of Classification Search
None
See application file for complete search history.

(56) References Cited

U.S. PATENT DOCUMENTS 5,006,158 A    4/1991    Carter et al.

OTHER PUBLICATIONS

Rosemblat et al., Melanosomal Defects in Melanocytes from Mice Lacking Expression of the Pink-Eyed Dilution Gene: Correction by Culture in the Presence of Excess Tyrosine, Exp. Cell Research, 239, 344-352 (1998).*
Sarangarajan et al., Tyrp1 and Oculocutaneous Albinism Type 3, Pigment Cell Res., 14: 437-444, 2001.*
Summers, Vision in albinism, Trans Am Ophthalmol Soc. 1996; 94: 1095-1155.*
Lock et al., Tissue distribution of 2-(2-nitro-4-trifluoromethylbenzoyl)-cyc]ohexane- 1,3-dione (NTBC) and its effect on enzymes involved in tyrosine catabolism in the mouse, Toxicology, 144 (1-3), 179-187 (2000).*
Sidman et al., Pink-eyed dilution (p) gene in rodents: Increased pigmentation in tissue culture, Developmental Biology, vol. 12, Issue 1, Aug. 1965, pp. 93-116.*
Lopez et al., L-DOPA Is an Endogenous Ligand for OA1, PLoS Biol. 2008; 6 (9): e236.*
Bennett et al., "Cloned mouse melanocyte lines carrying the germline mutations albino and brown: complementation in culture," *Development*, 105 (2), 379-385 (1989).
Brilliant, "The mouse p (pink-eyed dilution) and human P genes, oculocutaneous albinism type 2 (OCA2), and melanosomal pH," *Pigment Cell Res.*, 14 (2), 86-93 (2001).
Brooks et al., "Analysis of ocular hypopigmentation in Rab38cht/cht mice," *Invest. Ophthalmol. Vis. Sci.*, 48 (9), 3905-3913 (2007).
Garcia-Borron et al., "Molecular anatomy of tyrosinase and its related proteins: beyond the histidine-bound metal catalytic center," *Pigment Cell Res.*, 15 (3), 162-173 (2002).
Gaykema et al., "Structure determination of *Panulirus interruptus* haemocyanin at 3.2 a resolution. Successful phase extension by six-fold density averaging," *J. Mol. Biol.*, 187 (2), 255-275 (1986).
Green, *Mouse News Lett.*, 49, 31-33 (1973).
International Preliminary Report on Patentability, Application No. PCT/US2011/026260, dated Aug. 28, 2012.
International Search Report, Application No. PCT/US2011/026260, dated Apr. 4, 2011.
Klabunde et al., "Crystal structure of a plant catechol oxidase containing a dicopper center," *Nat. Struct. Biol.*, 5 (12), 1084-1090 (1998).
Kvittingen, "Tyrosinaemia—treatment and outcome," *J. Inherit. Metab. Dis.*, 18 (4), 375-379 (1995).
Laskowski et al., "PROCHECK: a program to check the stereochemical quality of protein structures," *J. Appl. Cryst.*, 26, 283-291 (1993).
Lee, "Predicting protein mutant energetics by self-consistent ensemble optimization," *J. Mol. Biol.*, 236 (3), 918-939 (1994).
Lindstedt et al., "Treatment of hereditary tyrosinaemia type I by inhibition of 4-hydroxyphenylpyruvate dioxygenase," *Lancet*, 340 (8823), 813-817 (1992).
Lock et al., "Tissue distribution of 2-(2-nitro-4-trifluoromethylbenzoy1)-cyclohexane-1,3-dione (NTBC) and its effect on enzymes involved in tyrosine catabolism in the mouse," *Toxicology*, 144 (1-3), 179-187 (2000).
Matoba et al., "Crystallographic evidence that the dinuclear copper center of tyrosinase is flexible during catalysis," *J. Biol. Chem.*, 281 (13), 8981-8990 (2006).
Needleman et al., "A general method applicable to the search for similarities in the amino acid sequence of two proteins," *J. Mol. Biol.*, 48 (3), 443-453 (1970).

(Continued)

Primary Examiner — Svetlana M. Ivanova
(74) Attorney, Agent, or Firm — Leydig, Voit & Mayer (57) ABSTRACT

A method is provided for the treatment of vision problems in a subject suffering from one of various forms of albinism, including, for example, oculocutaneous albinism types OCA1a and OCA1b, as well as ocular albinism type 1, resulting from mutations in the GPR143 gene, as well as the OCA2, OCA3 or OCA4 genes, by administering to the subject a pharmaceutical composition comprising a therapeutically effective amount of the compound (2-[2-nitro-4-(trifluoromethyl)benzoyl]cyclohexane-1,3-dione), also known as NTBC for a sufficient period of time. The administration of NTBC is believed to increase the amount of pigmentation in the subject and alleviate certain symptoms caused by lack of pigmentation in the eye tissues. Also described are methods of use of NTBC for increasing the pigmentation of a subject for cosmetic purposes, by administering to the subject a therapeutically effective amount of NTBC.

15 Claims, 8 Drawing Sheets

(56) References Cited

OTHER PUBLICATIONS

Olivares et al., "The 5,6-dihydroxyindole-2-carboxylic acid (DHICA) oxidase activity of human tyrosinase," *Biochem. J.*, 354 (Pt. 1), 131-139 (2001).

Onojafe et al., "Nitisinone improves eye and skin pigmentation defects in a mouse model of oculocutaneous albinism," *J. Clin. Invest.*, 121 (10), 3914-3923 (2011).

Pettersen et al., "USCF Chimera—a visualization system for exploratory research and analysis," *J. Comput. Chem.*, 25 (13), 1605-1612 (2004).

RCSB Protein Data Bank ID: 1bt3 "Catechol Oxidase from Ipomoea Batatas (Sweet Potatoes) in the Native CU(II)-CU(II) State," (printed Sep. 4, 2012).

RCSB Protein Data Bank ID: 2ah1 "Crystal structure of aromatic amine dehydrogenase (AADH) from *Alcaligenes faecalis*," (printed Sep. 4, 2012).

Rosemblat et al., "Melanosomal defects in melanocytes from mice lacking expression of the pink-eyed dilution gene: correction by culture in the presence of excess tyrosine," *Exp. Cell Res.*, 239 (2), 344-352 (1998).

Sarangarajan et al., "Tyrp1 and oculocutaneous albinism type 3," *Pigment Cell Res.*, 14 (6), 437-444 (2001).

Schiaffino et al., "Effective retrovirus-mediated gene transfer in normal and mutant human melanocytes," *Hum. Gene Ther.*, 13 (8), 947-957 (2002).

Schweikardt et al., "A three-dimensional model of mammalian tyrosinase active site accounting for loss of function mutations," *Pigment Cell Res.*, 20 (5), 395-401 (2007).

Sendovski et al., "First structures of an active bacterial tyrosinase reveal copper plasticity," *J. Mol. Biol.*, 405 (1), 227-237 (2011).

Slominski et al., "Differential expression and activity of melanogenesis-related proteins during induced hair growth in mice," *J. Invest. Dermatol.*, 96 (2), 172-179 (1991).

Suwannarat et al., "Use of nitisinone in patients with alkaptonuria," *Metabolism*, 54 (6), 719-728 (2005).

Suzuki et al., "Recent advances in genetic analyses of oculocutaneous albinism types 2 and 4," *J. Dermatol. Sci.*, 51 (1), 1-9 (2008).

\* cited by examiner

FIGURE 8

NITISINONE FOR TREATMENT OF OCULOCUTANEOUS/OCULAR ALBINISM AND FOR INCREASING PIGMENTATION

CROSS-REFERENCE TO RELATED APPLICATION

This application is a U.S. National Phase of International Patent Application No. PCT/US11/026260, filed Feb. 25, 2011, which claims the benefit of U.S. Provisional Application No. 61/308,771, filed on Feb. 26, 2010, the entire contents of each of which are incorporated by reference.

BACKGROUND OF THE INVENTION

Albinism (also called achromia, achromasia, or achromatosis) is a congenital disorder characterized by the complete or partial absence of pigment in the skin, hair, and eyes due to absence or defect of an enzyme involved in the production of melanin. Certain forms of albinism are known to be due to mutations in tyrosine metabolism. Albinism results from inheritance of recessive gene alleles and is known to affect all vertebrates, including humans. There is also known an X-linked form of albinism. Patients with albinism have significant visual disability.

In oculocutaneous albinism (OCA) (despite its Latin-derived name meaning "eye-and-skin" albinism), pigment is lacking in the eyes, skin, and hair. (The equivalent mutation in non-humans also results in lack of melanin in the fur, scales, or feathers.) People with oculocutaneous albinism can have anything from no pigment at all to near normal levels of pigmentation. There are at least three general types of OCA, characterized as Type 1, Type 2 and Type 3.

Oculocutaneous albinism type 1 (OCA1) is caused by a mutation in the tyrosinase gene, and can occur in two variations. Tyrosinase converts tyrosine to dihydroxyphenylalanine (DOPA) and DOPAquinone. The first type OCA1 mutation found was identified as OCA1a, resulting in an organism that cannot develop pigment at all. The hair is usually white (often translucent) and the skin very pale. Vision in an affected individual usually ranges from 20/200 to 20/400. A second known type OCA1 mutation is identified as type OCA1b, which itself has several subtypes. This is a less severe form of albinism and some affected individuals with OCA1b can actually tan and develop pigment in the hair.

Patients with albinism experience varying degrees of vision loss associated with foveal hypoplasia, nystagmus, photophobia and/or glare sensitivity, refractive errors, and abnormal decussation of ganglion cell axons at the optic chiasm. Current treatment options for vision problems caused by albinism are limited to correction of refractive errors and amblyopia, low vision aids, and (in some cases) extraocular muscle surgery.

Another form of albinism is ocular albinism. Ocular albinism is a genetic condition that primarily affects the eyes. In ocular albinism, only the eyes lack pigment. People who have ocular albinism have generally normal skin and hair color, although their coloration is typically lighter than either parent. Many even have a normal eye appearance. This condition reduces the coloring (pigmentation) of the iris, which is the colored part of the eye, and the retina, which is the light-sensitive tissue at the back of the eye. Pigmentation in the eye is essential for normal vision.

Ocular albinism is characterized by severely impaired sharpness of vision (visual acuity) and problems with combining vision from both eyes to perceive depth (stereoscopic vision). Although the vision loss is permanent, it does not worsen over time. Other eye abnormalities associated with this condition include rapid, involuntary eye movements (nystagmus), eyes that do not look in the same direction (strabismus), and increased sensitivity to light (photophobia). Many affected individuals also have abnormalities involving the optic nerves, which carry visual information from the eye to the brain.

Unlike some other forms of albinism, ocular albinism does not significantly affect the color of the skin and hair. People with this condition may have a somewhat lighter complexion than other members of their family, but these differences are usually minor.

Ocular albinism type 1 results from mutations in the GPR143 gene. This gene is responsible for making a protein that plays a role in pigmentation of the eyes and skin. The GPR143 gene helps control the growth of melanosomes, which are cellular structures that produce and store a pigment called melanin. Melanin is the substance that gives skin, hair, and eyes their color. In the retina, this pigment also plays a role in normal vision.

Most mutations in the GPR143 gene alter the size or shape of the GPR143 protein. Many of these genetic changes prevent the protein from reaching melanosomes to control their growth. In other cases, the protein reaches melanosomes normally, but mutations disrupt the protein's function. As a result of these changes, melanosomes in skin cells and the retina can grow abnormally large. Researchers are uncertain how these giant melanosomes are related to vision loss and other eye abnormalities in people with ocular albinism.

Currently, treatments for the visual impairment of oculocutaneous albinism are quite limited, and children with OCA may be left with vision approaching or reaching legal blindness. Even a modest effect on visual function (such as reduction of glare and light sensitivity) is greatly appreciated by patients.

As such, there exists a need for improving the treatment of patients, particularly for improving the vision of patients, suffering from various forms of albinism.

BRIEF SUMMARY OF THE INVENTION

Nitisinone (NTBC) is an FDA-approved drug used in the treatment of tyrosinemia, type 1. The drug blocks the normal degradation pathway of tyrosine, thus allowing greater circulating plasma levels of tyrosine. In accordance with the present invention, it was found that administration of NTBC to subjects (e.g., mice or humans) with certain forms of albinism, resulted in increased circulating tyrosine levels, an increase in tyrosinase activity, and, subsequently, increased pigmentation.

In an embodiment, the present invention provides a method for increasing tyrosine plasma concentrations in a subject suffering from oculocutaneous albinism, the method comprising administering to the subject a pharmaceutically acceptable composition comprising NTBC in a therapeutically effective amount. In an embodiment, an effective amount of NTBC is the amount administered to a subject that results in plasma concentrations of tyrosine in the subject increasing from about 7 micromolar ($\mu M$) to about 2 millimolar (mM). In a further embodiment, an effective amount of NTBC is the amount administered to a subject that results in plasma concentrations of tyrosine in the subject increasing from about 70 $\mu M$ to about 2 mM. In another embodiment, an effective amount of NTBC is the amount administered to a subject that results in plasma concentrations of tyrosine in the subject increasing from at least about 50 $\mu M$ to a range of about 300 $\mu M$. In a preferred embodiment, an effective amount of NTBC is the amount administered to a subject that results in plasma concentrations of tyrosine in the subject increasing from at least about 70 μM. In another embodiment, the therapeutically effective amount of NTBC administered to a subject is at least about 0.1 mg/kg/day, in some embodiments, in the range of between about 0.1 mg/kg/day to about 10 mg/kg/day. Preferably, in another embodiment, the therapeutically effective amount of NTBC administered to a subject is at least about 0.5 mg/kg/day to about 4 mg/kg/day. In another embodiment, the therapeutically effective amount of NTBC administered to a subject is about 1 mg/kg/day to about 2 mg/kg/day, preferably about 1 mg/kg/day.

In another embodiment, the present invention provides a method for increasing tyrosine plasma concentrations in a subject suffering from oculocutaneous albinism, wherein the albinism is identified as type OCA1a, or type OCA1b.

In another embodiment, the present invention provides a method for increasing tyrosine plasma concentrations in a subject suffering from ocular albinism, the method comprising administering to the subject a pharmaceutically acceptable composition comprising NTBC in a therapeutically effective amount. In an embodiment, an effective amount of NTBC is the amount administered to a subject that results in plasma concentrations of tyrosine in the subject increasing from about 7 μM to about 2 mM. In a further embodiment, an effective amount of NTBC is the amount administered to a subject that results in plasma concentrations of tyrosine in the subject increasing from about 70 μM to about 2 mM. In another embodiment, an effective amount of NTBC is the amount administered to a subject that results in plasma concentrations of tyrosine in the subject increasing from at least about 50 μM to a range of about 300 μM. In a preferred embodiment, an effective amount of NTBC is the amount administered to a subject that results in plasma concentrations of tyrosine in the subject increasing from at least about 70 μM. In another embodiment, the therapeutically effective amount of NTBC administered to a subject is at least about 0.1 mg/kg/day, in some embodiments, in the range of between about 0.1 mg/kg/day to about 10 mg/kg/day. Preferably, in another embodiment, the therapeutically effective amount of NTBC administered to a subject is at least about 0.5 mg/kg/day to about 4 mg/kg/day. In another embodiment, the therapeutically effective amount of NTBC administered to a subject is about 1 mg/kg/day to about 2 mg/kg/day, preferably about 1 mg/kg/day.

In yet another embodiment, the present invention provides a method for treating impaired vision in a subject suffering from oculocutaneous albinism, or ocular albinism, the method comprising administering to the subject a pharmaceutically acceptable composition comprising NTBC in a therapeutically effective amount. In an embodiment, an effective amount of NTBC is the amount administered to a subject that results in plasma concentrations of tyrosine in the subject increasing from about 7 μM to about 2 mM. In a further embodiment, an effective amount of NTBC is the amount administered to a subject that results in plasma concentrations of tyrosine in the subject increasing from about 70 μM to about 2 mM. In another embodiment, an effective amount of NTBC is the amount administered to a subject that results in plasma concentrations of tyrosine in the subject increasing from at least about 50 μM to a range of about 300 μM. In a preferred embodiment, an effective amount of NTBC is the amount administered to a subject that results in plasma concentrations of tyrosine in the subject increasing from at least about 70 μM. In another embodiment, the therapeutically effective amount of NTBC administered to a subject is at least about 0.1 mg/kg/day, in some embodiments, in the range of between about 0.1 mg/kg/day to about 10 mg/kg/day. Preferably, in another embodiment, the therapeutically effective amount of NTBC administered to a subject is at least about 0.5 mg/kg/day to about 4 mg/kg/day. In another embodiment, the therapeutically effective amount of NTBC administered to a subject is about 1 mg/kg/day to about 2 mg/kg/day, preferably about 1 mg/kg/day.

In a further embodiment, the present invention provides a method for increasing pigmentation in the eyes, hair and/or skin of a subject, the method comprising administering to the subject a pharmaceutically acceptable composition comprising NTBC in a therapeutically effective amount such that the plasma concentrations of tyrosine in the subject are increased to an amount sufficient to increase visually discernable pigmentation in the subject.

DETAILED DESCRIPTION OF THE INVENTION

In an embodiment, the present invention provides a method for increasing tyrosine plasma concentrations in a subject suffering from oculocutaneous albinism, the method comprising administering to the subject a pharmaceutically acceptable composition comprising NTBC in a therapeutically effective amount. In an embodiment, an effective amount of NTBC is the amount administered to a subject that results in plasma concentrations of tyrosine in the subject increasing from about 7 μM to about 2 mM. In a further embodiment, an effective amount of NTBC is the amount administered to a subject that results in plasma concentrations of tyrosine in the subject increasing from about 70 µM to about 2 mM. In another embodiment, an effective amount of NTBC is the amount administered to a subject that results in plasma concentrations of tyrosine in the subject increasing from at least about 50 µM to a range of about 300 µM. In a preferred embodiment, an effective amount of NTBC is the amount administered to a subject that results in plasma concentrations of tyrosine in the subject increasing from at least about 70 µM. In another embodiment, the therapeutically effective amount of NTBC administered to a subject is at least about 0.1 mg/kg/day, in some embodiments, in the range of between about 0.1 mg/kg/day to about 10 mg/kg/day. Preferably, in another embodiment, the therapeutically effective amount of NTBC administered to a subject is at least about 0.5 mg/kg/day to about 4 mg/kg/day. In another embodiment, the therapeutically effective amount of NTBC administered to a subject is about 1 mg/kg/day to about 2 mg/kg/day, preferably about 1 mg/kg/day.

In another embodiment, the present invention provides a method for increasing tyrosine plasma concentrations in a subject suffering from oculocutaneous albinism, for example, wherein the albinism is identified as type OCA1a, meaning the affected subject has no measurable tyrosinase activity, or type OCA1b, meaning the affected subject has greatly diminished tyrosinase activity. It is contemplated that other foams of oculocutaneous albinism can be treated by the methods of the present invention.

In yet another embodiment, the present invention provides a method for increasing tyrosine plasma concentrations in a subject suffering from ocular albinism, the method comprising administering to the subject a pharmaceutically acceptable composition comprising NTBC in a therapeutically effective amount. In an embodiment, an effective amount of NTBC is the amount administered to a subject that results in plasma concentrations of tyrosine in the subject increasing from about 7 µM to about 2 mM. In a further embodiment, an effective amount of NTBC is the amount administered to a subject that results in plasma concentrations of tyrosine in the subject increasing from about 70 µM to about 2 mM. In another embodiment, an effective amount of NTBC is the amount administered to a subject that results in plasma concentrations of tyrosine in the subject increasing from at least about 50 µM to a range of about 300 µM. In a preferred embodiment, an effective amount of NTBC is the amount administered to a subject that results in plasma concentrations of tyrosine in the subject increasing from at least about 70 µM. In another embodiment, the therapeutically effective amount of NTBC administered to a subject is at least about 0.1 mg/kg/day, in some embodiments, in the range of between about 0.1 mg/kg/day to about 10 mg/kg/day. Preferably, in another embodiment, the therapeutically effective amount of NTBC administered to a subject is at least about 0.5 mg/kg/day to about 4 mg/kg/day. In another embodiment, the therapeutically effective amount of NTBC administered to a subject is about 1 mg/kg/day to about 2 mg/kg/day, preferably about 1 mg/kg/day.

In yet another embodiment, the present invention provides a method for treating impaired vision in a subject suffering from oculocutaneous albinism, or ocular albinism, the method comprising administering to the subject a pharmaceutically acceptable composition comprising NTBC in a therapeutically effective amount. In an embodiment, an effective amount of NTBC is the amount administered to a subject that results in plasma concentrations of tyrosine in the subject increasing from about 7 µM to about 2 mM. In a further embodiment, an effective amount of NTBC is the amount administered to a subject that results in plasma concentrations of tyrosine in the subject increasing from about 70 µM to about 2 mM. In another embodiment, an effective amount of NTBC is the amount administered to a subject that results in plasma concentrations of tyrosine in the subject increasing from at least about 50 µM to a range of about 300 µM. In a preferred embodiment, an effective amount of NTBC is the amount administered to a subject that results in plasma concentrations of tyrosine in the subject increasing from at least about 70 µM. In another embodiment, the therapeutically effective amount of NTBC administered to a subject is at least about 0.1 mg/kg/day, in some embodiments, in the range of between about 0.1 mg/kg/day to about 10 mg/kg/day. Preferably, in another embodiment, the therapeutically effective amount of NTBC administered to a subject is at least about 0.5 mg/kg/day to about 4 mg/kg/day. In another embodiment, the therapeutically effective amount of NTBC administered to a subject is about 1 mg/kg/day to about 2 mg/kg/day, preferably about 1 mg/kg/day.

In a further embodiment, the present invention provides a method of treating oculocutaneous albinism, or ocular albinism, the method comprising administering to the subject a pharmaceutically acceptable composition comprising NTBC in a therapeutically effective amount. In addition, the methods disclosed herein are not limited to oculocutaneous albinism, or ocular albinism, but can be used for subjects having other forms of albinism, including, but not limited to, for example, albinism which results from mutations in the microtubulin associated protein tau (MATP, OCA4) gene, the P protein gene (OCA2) (See, Brilliant, M. H., *Pigment Cell Res.*, 14:86-93 (2001)), and in the tyrosine related protein 1 (TYRP1, OCA3) gene (See, Sarangarajan, R. et al., *Pigment Cell Res.*, 14:437-44 (2001)).

In a further embodiment, the present invention provides a method for increasing pigmentation in the eyes, hair, and/or skin of a subject, the method comprising administering to the subject a pharmaceutically acceptable composition comprising NTBC in a therapeutically effective amount such that the plasma concentrations of tyrosine in the subject are increased to an amount sufficient to increase visually discernable pigmentation in the subject. In this embodiment, the use of NTBC to increase skin, eye, or hair pigmentation, is for cosmetic purposes.

In accordance with the present invention, in an embodiment, the present invention provides a pharmaceutical composition comprising 2-(-2-nitro-4 trifluoromethylbenzoyl)-1,3 cyclohexanedione (NTBC) or a pharmaceutically acceptable salt, hydrate, or solvate thereof, wherein the composition includes a pharmaceutically and physiologically acceptable carrier, in an amount effective for use in a medicament, preferably for use as a medicament for treating impaired vision in the eyes of a subject suffering from oculocutaneous albinism, or for use as a medicament for treating impaired vision in the eyes a subject suffering from ocular albinism, or for use as a medicament for increasing pigmentation in the eyes, hair, or skin of a subject, when administered to the subject in an effective amount. In an embodiment, an effective amount of NTBC is the amount administered to a subject that results in plasma concentrations of tyrosine in the subject increasing from about 7 µM to about 2 mM. In a further embodiment, an effective amount of NTBC is the amount administered to a subject that results in plasma concentrations of tyrosine in the subject increasing from about 70 µM to about 2 mM. In another embodiment, an effective amount of NTBC is the amount administered to a subject that results in plasma concentrations of tyrosine in the subject increasing from at least about 50 µM to a range of about 300 µM. In a preferred embodiment, an effective amount of NTBC is the amount administered to a subject that results in plasma concentrations of tyrosine in the subject increasing from at least about 70 µM. In another embodiment, the therapeutically effective amount of NTBC administered to a subject is at least about 0.1 mg/kg/day, in some embodiments, in the range of between about 0.1 mg/kg/day to about 10 mg/kg/day. Preferably, in another embodiment, the therapeutically effective amount of NTBC administered to a subject is at least about 0.5 mg/kg/day to about 4 mg/kg/day. In another embodiment, the therapeutically effective amount of NTBC administered to a subject is about 1 mg/kg/day to about 2 mg/kg/day, preferably about 1 mg/kg/day.

It is also contemplated that the pharmaceutical composition of the present invention can be used to treat subjects having type OCA1a oculocutaneous albinism, and/or type OCA1b oculocutaneous albinism and/or type 1 ocular albinism.

In another embodiment, the present invention provides a pharmaceutical composition comprising 2-(-2-nitro-4 trifluoromethylbenzoyl)-1,3 cyclohexanedione (NTBC) or a pharmaceutically acceptable salt, hydrate, or solvate thereof, wherein the composition includes a pharmaceutically and physiologically acceptable carrier, in an amount effective for use in a medicament, preferably for use as a medicament for treating impaired vision in the eyes of a subject suffering from oculocutaneous albinism, or for use as a medicament for treating impaired vision in the eyes a subject suffering from ocular albinism, or for use as a medicament for increasing pigmentation in the eyes, hair, or skin of a subject, when administered to the subject in an effective amount, when the subject is suffering from albinism due to a mutation in the P protein gene (OCA2), and/or the tyrosinase-related protein-1 (TYRP-1, OCA3), and/or the microtubulin associated protein tau (MATP, OCA4) gene.

Figure 1:
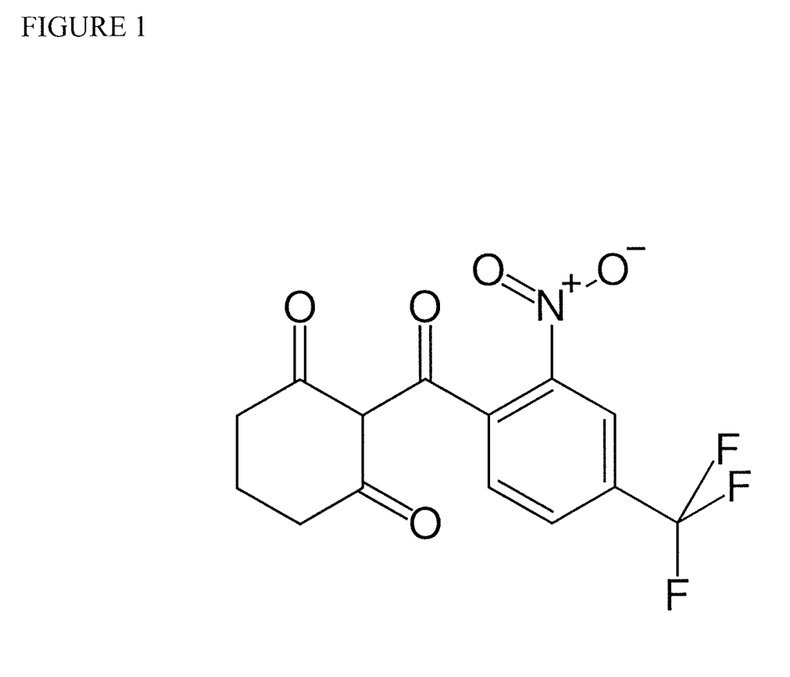
FIG. 1 is the chemical structure of NTBC.

NTBC is marketed as Orfardin®, which was designated an orphan drug in May 1995 by the FDA, for the treatment of a rare inherited disorder of intermediate metabolism, type 1 tyrosinemia, in which patients are unable to properly break down the amino acid tyrosine (FIG. 1). The synthesis and use of NTBC, and its related compounds, as an herbicide, is described in U.S. Pat. No. 5,006,158.

Figure 2:
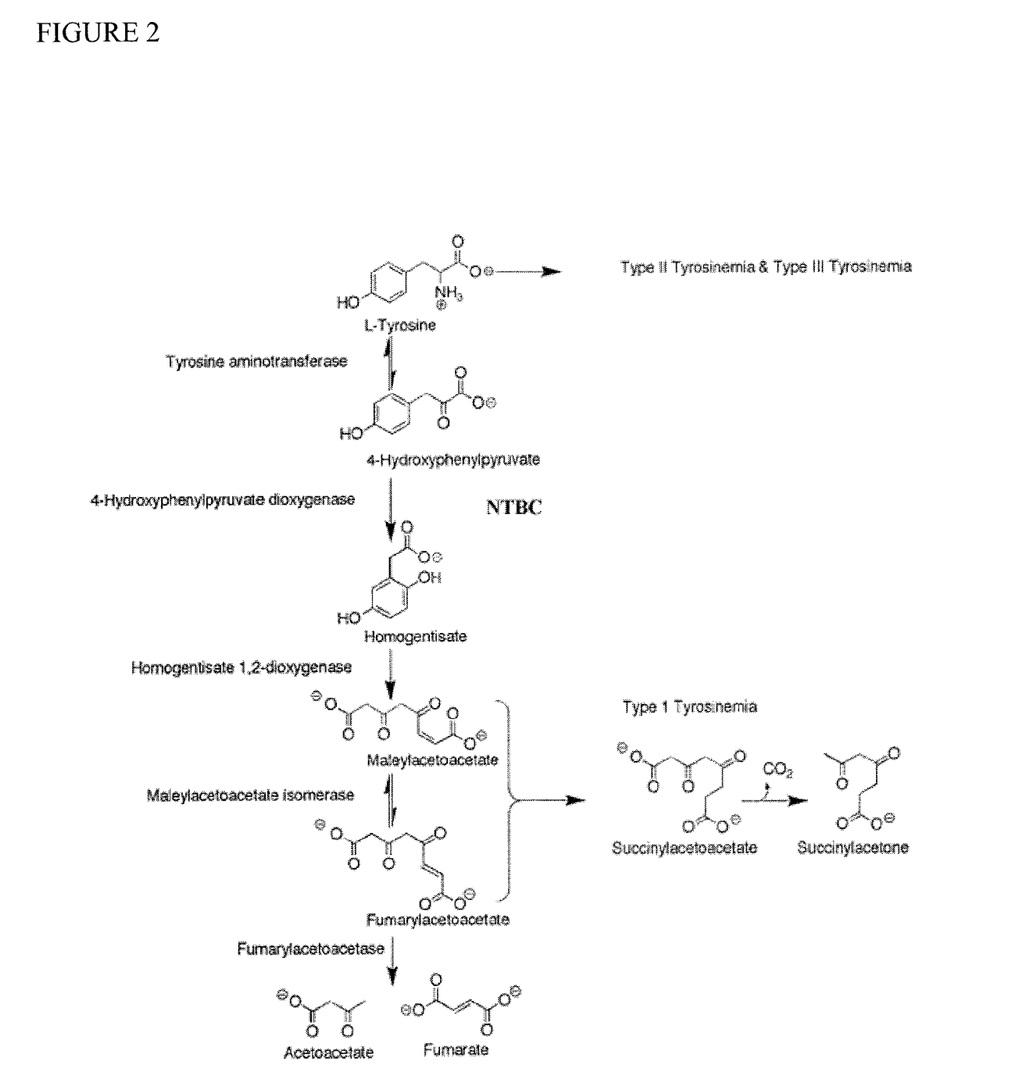
FIG. 2 shows the metabolic pathway for tyrosine degradation in mammals and where NBTC blocks the enzyme 4-hydroxyphenyl-pyruvate dioxygenase early in the pathway.

NTBC blocks the enzyme parahydroxyphenylpyruvic acid dioxygenase (p-HPPD), the second step in the tyrosine degradation pathway, prevents the accumulation of fumarylacetoacetate and its conversion to succinylacetone (FIG. 2).

Because NTBC increases the concentration of tyrosine in the blood, dietary management with controlled intake of phenylalanine and tyrosine should considered immediately upon diagnosis, to prevent tyrosine crystals from forming in the cornea of subjects undergoing NTBC therapy. If the blood concentration of phenylalanine becomes too low (<20 µM), additional protein should be added to the diet.

In those embodiments where the route of administration is other than oral, the therapeutic compositions of the present invention generally are placed into a container having a sterile access port, for example, an intravenous solution bag or vial having a stopper pierceable by a hypodeimic injection needle. The route of administration of NTBC, in accordance with the present invention, is in accord with known methods, e.g., oral ingestion, injection or infusion by intravenous, intraperitoneal, intramuscular, intrarterial, subcutaneous, intralesional routes, by aerosol or intranasal routes, or by sustained release systems as noted below. NTBC can be administered continuously by infusion or by bolus injection.

The term "treat" as well as words stemming therefrom, as used herein, do not necessarily imply 100% or complete treatment. Rather, there are varying degrees of treatment of which one of ordinary skill in the art recognizes as having a potential benefit or therapeutic effect. In this respect, the inventive methods can provide any amount of any level of treatment of albinism in a subject. Furthermore, the treatment provided by the inventive method can include treatment of one or more conditions or symptoms of the albinism being treated.

An effective amount of NTBC to be employed therapeutically will depend, for example, upon the therapeutic and treatment objectives, the route of administration, the age, condition, and body mass of the patient undergoing treatment or therapy, and auxiliary or adjuvant therapies being provided to the patient. Accordingly, it will be necessary and routine for the practitioner to titer the dosage and modify the route of administration, as required, to obtain the optimal therapeutic effect. A typical daily dosage might range from at least about 0.1 mg/kg/day to up to about 100 mg/kg/day or more, preferably from about 0.1 to about 10 mg/kg/day depending on the above-mentioned factors. Typically, the clinician will administer antibody until a dosage is reached that achieves the desired effect. The progress of this therapy is easily monitored by conventional assays.

The dosage ranges for the administration NTBC are those large enough to produce the desired effect in which the visual symptoms of albinism, such as nystagmus, photosensitivity or strabismus are ameliorated. The dosage should not be so large as to cause adverse side effects, such as unwanted cross-reactions, anaphylactic reactions, and the like. Generally, the dosage will vary with the age, condition, sex and extent of disease of the patient and can be determined by one of skill in the art. The dosage can be adjusted by the individual physician in the event of any complication. In an embodiment, the methods of the present invention provide for the administration of NTBC to children suffering from albinism, ranging in age from six months to 6 years old. In another embodiment, the methods of the present invention provide for the administration of NTBC to adults suffering from albinism.

NTBC is generally prescribed to patients suffering from oculocutaneous albinism or ocular albinism at dosages of about 1.0 mg/kg/day; however, individual doses may vary. For example, dosages may be from at least about 0.1 mg/kg/day to about 10 mg/kg/day, or preferably, from about 0.5 mg/kg/day to about 5 mg/kg/day. Dosage should be adjusted to maintain plasma tyrosine concentrations between at least about 10 µM, to concentrations in the millimolar range. For example, plasma tyrosine concentrations between at least about 50 µM, to about 2 mM, or for example, plasma tyrosine concentrations between at least about 70 µM to about 1 mM, or for example, plasma tyrosine concentrations between about 200 µM to about 500 µM. It is contemplated that the therapeutically effective dosage is one that theoretically blocks greater than 99% of p-HPPD activity.

NTBC can be administered orally, intravenously, intraperitoneally, intramuscularly, subcutaneously, intracavity, or transdermally, alone or in combination with other drugs. Preferably, NTBC is administered orally by capsule or pill form. It is understood that the pills formulated for oral administration, including pills used in the present invention, may contain ingredients to serve as fillers, binders and for color coding purposes. These ingredients are in common use in many oral formulations and may include, but are not limited to, lactose, corn starch, calcium phosphate, povidone, magnesium stearate, stearic acid, colloidal silicon dioxide, hydroxypropyl methylcellulose, polyethylene glycol and one or more of the following dyes: FD&C Blue No. 1 Lake, FD&C Blue No. 2 Aluminum Lake, D&C Green No. 5, D&C Yellow No. 10, FD&C Yellow No. 6 or FD&C Red No. 3. Of course, these are only exemplary fillers and dyes, those of skill in the art will recognize that other inactive ingredients may be used in the preparation of the formulations of the present invention.

Preparations for parenteral administration include, for example, sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include, for example, water, alcoholic/aqueous solutions, emulsions or suspensions, including saline and buffered media. Parenteral vehicles include, for example, sodium chloride solution, Ringer's dextrose, dextrose and sodium chloride, lactated Ringer's, or fixed oils. Intravenous vehicles include, for example, fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Injectable formulations are also in accordance with the invention. The requirements for effective pharmaceutical carriers for injectable compositions are well-known to those of ordinary skill in the art (see, e.g., *Pharmaceutics and Pharmacy Practice,* J. B. Lippincott Company, Philadelphia, Pa., Banker and Chalmers, eds., pages 238-250 (1982), and *ASHP Handbook on Injectable Drugs, Trissel,* 15th ed., pages 622-630 (2009)).

Preferably, the carrier is a pharmaceutically acceptable carrier. With respect to pharmaceutical compositions, the carrier can be any of those conventionally used and is limited only by chemico-physical considerations, such as solubility and lack of reactivity with the active compound(s), and by the route of administration. The pharmaceutically acceptable carriers described herein, for example, vehicles, adjuvants, excipients, and diluents, are well-known to those skilled in the art and are readily available to the public. It is preferred that the pharmaceutically acceptable carrier be one which is chemically inert to the active agent(s) and one which has no detrimental side effects or toxicity under the conditions of use.

Preservatives and buffers may be used. In order to minimize or eliminate irritation at the site of injection, such compositions may contain, for example, one or more nonionic surfactants having a hydrophile-lipophile balance (HLB) of, illustratively, from about 12 to about 17. The quantity of surfactant in such formulations will typically range from about 5% to about 15% by weight. Suitable surfactants include, for example, polyethylene glycol sorbitan fatty acid esters, such as sorbitan monooleate and the high molecular weight adducts of ethylene oxide with a hydrophobic base, formed by the condensation of propylene oxide with propylene glycol. The formulations can be presented in unit-dose or multi-dose sealed containers, such as ampoules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets.

In an embodiment, NTBC is given orally in two divided doses; however, because of the long half-life (50-60 hours), affected individuals who are older and more stable may maintain adequate therapy with once-per-day dosing. For example, dosages can be given once a day, or once every other day.

EXAMPLES

The following examples further illustrate the invention but, of course, should not be construed as in any way limiting its scope.

Animal Husbandry and Clinical Examination. C57BL/6J mice (Stock #000664), C57BL/6JTyr$^{c-2J/c-2J}$ mice (Stock #000058, MGI ID #1855985), and C57BL/6Tyr$^{c-h/c-h}$ (Stock #000104, MGI ID #1855979) were obtained from the Jackson Laboratory (Bar Harbor, Me.). Mice were housed according to the institutional Animal Review Board standards with a 14 hour light/10 hour dark cycle. These studies conformed to the principles for laboratory animal research outlined by the Animal Welfare Act (NIH/HHS) and the ARVO Statement for the Use of Animals in Ophthalmic and Vision Research and were approved by the Institutional Animal Care and Use Committee of the National Eye Institute. Clinical examination and imaging of the anterior segment of mice were performed on gently-restrained, awake mice using a Haag-Streit BQ slit lamp and Imaging Module IM900® software (Haag-Streit, Inc., Mason, Ohio). Clinical examination of the posterior segment was performed on gently restrained, awake mice after dilation with one drop of 1% tropicamide (Alcon Laboratories, Inc., Fort Worth, Tex.) using an indirect ophthalmoscope (Keeler, Windsor, Berkshire, UK) with a 90D condensing lens (Volk, Mentor, Ohio). Fundus images were obtained on mice sedated with intraperitoneally injected 100 mg/ml ketamine, 200 mg/ml xylazine diluted in normal saline. Images were obtained using a Nikon D.90 digital SLR camera with a Nikon 85 mm f/2.8D micro AF-S ED lens mounted to a custom-made aluminum stand, using a 5 cm long Hopkins rigid otoscope coupled to a Xenon Nova light source (175 watt) and fiberoptic cable (Karl Storz, Tuttlingen, Germany). Mice were euthanized with carbon dioxide according to institutional guidelines.

Drug Dosing and Monitoring. Ten C57BL/6JTyr$^{e-2J/c-2J}$ and ten C57BL/6Tyr$^{c-h/c-h}$ mice, 3-4 months of age were designated for treatment with NTBC (Swedish Orphan Drug, Stockholm, Sweden). An equal number of age-matched controls of each genotype designated to receive vehicle treatment. NTBC was dissolved in 2 M NaOH and brought to neutral pH before administration to mice. Coat color, iris transillumination and fundus appearance were photodocumented prior to treatment. Because pigment deposition in hair is stimulated with new hair growth, a section of each mouse's coat was shaved prior to the beginning of the experiment. Drug or vehicle was given every other day via oral gavages, at a dosage of about 4 mg/kg, in a volume of about 0.2-0.3 ml. This dose of NTBC was chosen to give plasma tyrosine concentrations in the range of about 0.3-0.7 mM, or approximately two to four times the doses typically used in humans with tyrosinemia type 1, and within the limits of the maximally tolerated dose in mice. Coat color, iris transillumination and fundus appearance were photodocumented at the end of 1 month of treatment or vehicle dosing. For prenatal treatment experiments, pregnancy was determined by a maternal weight gain of ≥2 g over 7-9 days, after observing a vaginal mucus plug. Treatment with 4 mg/kg NTBC was initiated daily at day 9 or 10 of pregnancy by oral gavage, and given until birth of the litter. At that point, every-other-day oral treatment of the mother was initiated until time of weaning.

Plasma tyrosine was assayed from retro-orbital blood taken from mice at 1 week, and 4 weeks into treatment. Because the volume of blood that could be obtained from non-terminal bleeds was small, the plasma from 2-3 mice was pooled to make a single measurement. Plasma samples were frozen immediately after collection on dry ice. Samples ready for assay were gently thawed, diluted with an equal volume of loading buffer (0.2 M lithium citrate, pH 2.2), and filtered using Vivaspin 500 (3000 Da molecular weight cut-off, Sartorius Stedman Biotech, Göettingen, Germany) spun in a fixed angle centrifuge at about 14000×g for 60 minutes at a temperature of about 16-20° C. The supernatant was collected and tyrosine was quantitated on a Biochrom 30 spectrophotometer (Biochrom, Ltd., Cambridge, UK) using the manufacturer's specifications.

Transmission Electron Microscopy. Eyes from drug and vehicle-treated mice were dissected and divided into anterior and posterior segments (n=2 eyes from 2 separate mice in each group). The iris and posterior part (choroid, RPE and retina) of the eyes were removed and fixed in 2% glutaraldehyde and 2% paraformaldehyde in 0.1 M sodium phosphate buffer (PB), pH 7.4 for about 12 hours at room temperature (RT). After a wash with rinsing buffer (RB, 4% sucrose and 0.15 mM $CaCl_2$ in PB), pH 7.4 at 4° C., tissues were postfixed in 1% $OsO_4$ in 0.1 M PB, pH 7.4 for 1 hour. After rinsing and dehydration, tissues were embedded in Durcupan resin for 72 hours at 60° C. One micron semi-sections were used for tissue orientation. About 70-90 nm ultrasections were also collected in 200 mesh grids and counterstained with 5% uranyl acetate and 0.3% lead citrate. Sections were viewed on a JEOL 1010 transmission electron microscope at 60 KV (JEOL Korea, Ltd., Seoul, KR) and digital images were acquired at about 8000× to about 30,000× magnification by AMT software (Advanced Microscopy Techniques, Corp., Danvers, Mass.).

Structural Modeling. The atomic structures of the mouse tyrosinase have been modeled using the crystal coordinates of two bicopper-binding tyrosinase proteins from the RCSB protein data bank (http://www.pdb.org/pdb) as structural templates: 1) *Streptomyces Castaneoglobisporus* tyrosinase complexed with a caddie protein [Protein Data Bank ID: 2ahl]; and 2) the *Ipomea Batatas* sweet potato catechol (O-diphenol) oxidase containing dicopper center [Protein Data Bank ID: 1bt3]) (E. Abola, et al., in *Crystallographic Ddatabases-Information Content, Software Systems, Scientific Applications*, G. Bergerhoff, R. Sievers, Eds. (Data Comission on the International Union of Crystallography, Cambridge, 1987), pp. 107-132). Briefly, the structural alignment of these proteins was performed using the MatchMaker module incorporated in the UCSF Chimera, build 1.4.1 (E. F. Pettersen et al., *J Comput. Chem.*, 25:1605 (2004)). Primary sequences were aligned using the method of Needleman and Wunsch (S. B. Needleman & C. D. Wunsch, *J. Mol. Biol.*, 48:443 (1970)) integrated in the program Look, version 3.5.2 for tertiary structure prediction (C. Lee, *J. Mol. Biol.*, 236:918 (1994)). The conformation of the missense variants, R77L and H420R, was generated by the same program implicating a self-consistent ensemble optimization (500 cycles).

In Vitro Expression and Enzyme Activity. The expression construct of mouse Tyr was a kind gift of Dr. C. Olivares from the School of Medicine of the University of Murcia (Spain). This construct was prepared in the pcDNA3.1 expression vector (Invitrogen, Carlsbad, Calif.) using EcoRI/XbaI restriction sites and based on the mouse Tyr clone obtained as described previously in C. Olivares, et al., *Biochem. J.*354: 131 (2001). Constructs of tyrosinase gene mutant variants, with changes corresponding to missense mutations R77L and H420R in the mouse tyrosinase protein sequence, were created using standard methodologies (Mutagenex Inc., Piscataway, N.J.). All mutational changes were verified by the cDNA sequencing. Protein lysates for the wild type mouse tyrosinase, R77L and H420R missense variants were electrophoretically separated under reducing conditions, blotted, and then probed with αPEP7 antiserum, directed against the C-terminal cytosolic extension of Tyr. The αPEP7 antiserum was a generous gift from Dr. V. J. Hearing from the National Cancer Institute, National Institutes of Health, Bethesda, Md.

Chinese hamster ovary cells (CHO) (generous gift from Dr. J. T. Wroblewski from the Pharmacology Department, Georgetown University Medical Center, Washington D.C.) were grown at a temperature of about 37° C. in DMEM media, in the presence of 10% fetal bovine serum, 1% penicillin and 4.5 g proline per 0.5 liter of media. CHO cells were transfected with either mouse tyrosinase or mutant variants, using the pcDNA3.1 expression vector and Lipofectamine LTX reagent according to the manufacturer's instructions (Invitrogen, Calif.). In the cyclohexamide (CHX) experiments, cells were treated with CHX (2 µg/ml) or pretreated with tyrosine (1 mM) for 24 hours before addition of CHX in the time-course assay (0, 1, 3, 6, 9, and 24 hours). Following the treatment period, cells were harvested with lysis buffer (10 mM sodium phosphate, pH 7.0, 1% Igepal—CA630, protease inhibitor), and microfuged for 30 minutes at 13,200×g, at a temperature of about 4° C., to obtain a protein lysate. The total protein content in protein lysates was determined spectrophotometrically as a 280/260 ratio. Protein expression was analyzed by Western blotting, and GAPDH was used as an internal loading control. For the analysis, Western blots were scanned, intensities of protein bands were determined, and ratios of band intensities for the wild type or mutant variants, to that of GAPDH were calculated. Care was taken in choosing non-saturated images for analysis.

Melan-c cell cultures. Melan-c cells (melanocytes derived from mice homozygous for the albino mutation (D. C. Bennett et al., *Development*, 105:379 (1989)) were cultured in RPMI 1640, pH 6.9 supplemented with 5% fetal bovine serum (FBS), streptomycin-penicillin (100 µg/ml each), 200 nM tetradeconyl phorbol acetate (TPA), and 100 µM β-mercaptoethanol, at 37° C. in 10% $CO_2$. Cells were transfected using Fugene HD reagent according to the manufacturer's instructions (Roche Diagnostics Inc., Indianapolis, Ind.) in presence or absence of 1 mM tyrosine. After 24 hours, cells were washed twice with saline phosphate buffer, harvested in 10 mM sodium phosphate, pH 6.8, containing 1% Igepal CA-630 and protease inhibitor (Roche), and microcentrifuged for 30 minutes at 13,200×g, at a temperature of about 4° C. to obtain a protein lysate.

Diphenol oxidase activity of tyrosinase was determined spectrophotometrically according to Slominski et al., *J. Invest. Dermatol.*, 96:172 (1991), with minor modifications. Briefly, the reaction mixtures contained 7 mM L-dopa in 0.1 M sodium phosphate buffer (pH 6.8) and protein lysate (20 mg/ml) was incubated at 37° C. and monitored by measuring the absorbance at 475 nm. All experiments were conducted in triplicate.

Human melanocyte culture and melanin assay. Human melanocytes were established from skin punch biopsies. Skin specimens were washed with PBS then treated with 0.25% trypsin-EDTA (Gibco 25200) for about 2 hours followed by vigorous vortexing to separate the epidermis. The epidermis was sectioned and attached to scored patches on the bottom of a 6-well polystyrene culture dish before being covered with melanocyte media. About 1000 ml of melanocyte media was made from 950 ml Ham's F10 (Gibco 1550), 25 ml FBS, 5 ug bFGF (Sigma F0291), 10 ug endothelin (Sigma, E7764, Sigma Chemicals, St. Louis, Mo.), 7.5 mg IBMX (Sigma 17018), 30 µg cholera toxin (Sigma C8052), 3.3 µg TPA (Sigma P8139), 10 ml PenStrepGlutamine, 1 ml fungizone and the media was 0.22 µm filtered.

Melanocytes were plated on 6 well dishes and grown to confluency. Melanin assays were run in triplicate by supplementing three wells per plate with 1 mM tyrosine (Sigma T8566), using the remaining 3 wells as untreated controls. Treatment time was approximately one week. Melanocytes from each well were harvested separately by trypsinization and washed twice with 1× PBS. Pellets were resuspended in 400 µl of 1× PBS and sonicated briefly. The lysate was then split to an equal volume of 2 N NaOH (300 µl) and incubated at 80° C. for 1 hour to solubilize melanin. The $OD_{475}$ was measured and converted to melanin content via a standard curve using synthetic melanin (Sigma M0418). The data were nomialized to protein content, determined using a bicinchoninic (BCA) assay kit (BioRad, Inc., Hercules, Calif.). Differences between treated and untreated measurements were analyzed with a two-tailed unpaired t-test.

Study Participants. Research subjects with OCA were ascertained via an IRB-approved clinical research protocol at the National Human Genome Institute, National Institutes of Health. Human research was in compliance with the Declaration of Helsinki. OCA-1A and OCA-1B were defined on clinical grounds based on hair, eye, and skin coloration at the time of first clinical exam. In addition to decreased pigmentation in the hair and skin, both patients had ophthalmic abnormalities consistent with albinism, including iris transillumination, nystagmus, decreased visual acuity, and an albinotic fundus, with no clear foveal reflex. Molecular confirmation included sequencing of the genes for OCA types 1 and 2 (TYR and OCA2 respectively). The OCA-1A subject had two known disease-causing mutations in TYR (c.230A>G, c.242C>T) and no likely disease-causing variants in OCA2. The OCA1B subject had one known disease-causing variant (c.229T>A) in TYR, and no likely disease-causing mutation in OCA2 (up to 63% of OCA2B patients have no second identifiable TYR mutation).

Example 1

This example demonstrates tests the effect of clinically-relevant doses of NTBC in a mouse model of oculocutaneous albinism, type 1a, (C57BL/6J-$Tyr^{c-2J/c-2J}$)using predefined ocular, systemic and biochemical outcome variables.

C57BL6/J-$Tyr^{c-2J/c-2J}$ mice are phenotypically albino due to a G291T (Arg77Leu) mutation in the Tyr gene that is functional null at the protein level (Green, E. L., *Mouse News Lett.*, 49:31 (1973)). These mice have a white coat color and pink eyes, and lack any significant fundus pigmentation. As such, they are a reasonable model for oculocutaneous albinism type OCA1a. Although these mice are completely albino, the mutation in their tyrosinase gene is a missense mutation. This leaves open the possibility that elevated tyrosine may stabilize the enzyme and improve flux through pigment production pathways. To minimize the effect of additional genetic factors on phenotype, both lines of mice used in these experiments are on the same inbred C57BL6/J background.

At the beginning of the study, baseline plasma concentrations of tyrosine, coat color (gross and microscopic), anterior segment pigment, and posterior segment pigment were documented for each mouse prior to initiating experiments. At least ten C57BL6/J-$Tyr^{c-2J/c-2J}$ mice, age 3-4 months, were treated with about 25 µg NTBC in a volume of about 0.2-0.3 ml, every other day, via oral gavage for a four-week period. These treated mice were compared to an age- and gender-matched cohort of C57BL6/J-$Tyr^{c-2J/c-2J}$mice over the same time period. The efficacy and safety of NTBC at this dose was previously demonstrated in other murine models. It is known that a possible side effect of NTBC treatment is corneal irritation, which is monitored daily. At the start of treatment, an area of hair was plucked or shaved from each mouse's back, which has the effect of stimulating new hair growth and possibly new pigment deposition in the hair shaft. At the end of four weeks time, plasma tyrosine concentrations were assessed in both treated and control animals.

Assessment of the effect treatment and the end of the experimental time period commenced with photodocumentation of coat color, anterior segment pigment and posterior segment pigment of each mouse. The mice were sacrificed using standard $CO_2$ euthanasia protocol. One eye from each mouse was submitted for light microscopy, while the other was prepared for electron microscopy. Liver and kidney tissues were collected and processed for light microscopy histology, to insure no pathology is associated with treatment. Additional blood samples were taken and frozen at the time of euthanasia, for possible future studies. Hair shafts in plucked and non-plucked areas were examined and photographed under light microscopy. Melanosome number and size was quantified in the retinal pigmented epithelial cells (RPE) and choroid of the posterior pole of both treated and untreated mice, in a masked fashion, as previously described by our group (Brooks, B. P., et al., *Invest. Ophthalmol. Vis. Sci.*, 48(9):3905-13 (2007)).

Results. The initial animal protocol started with a dose of 1 mg/kg of NTBC given to $Tyr^{c-2J/c-2J}$ mice, every other day, by oral gavage, a dose similar to that given to humans with tyrosinemia, type 1. Ten $Tyr^{c-2J/c-2J}$ were treated and plasma tyrosine levels were ascertained after one month. At this dose, over this interval, no phenotypic changes were noted and plasma tyrosine concentrations were not statistically significantly different between treated and control animals.

Toxicologic studies show that male Alpk:ApfCD-1 albino mice (age 3-6 weeks tolerate NTBC doses up to 160 mg/kg/day (Lock, E. A., et al., *Toxicology*, 144:179-187 (2000)). Maximum plasma tyrosine concentrations were achieved at or below 10 mg/kg NTBC. The dosing of NTBC in the two mouse models was increased to 4 mg/kg orally, every other day. Plasma tyrosine measurements of control and treated animals are presented in Table 1, below. NTBC treatment resulted in approximately a 6-fold increase in steady-state plasma tyrosine concentrations in $Tyr^{c-2J/c-2J}$ mice.

The coat color was compared to representative control, and treated mice, at the end of the trial. Although plasma tyrosine levels were elevated approximately 6-fold, there was no difference in coat color, fundus pigmentation, or iris transillumination in $Tyr^{c-2J/c-2J}$ mice. There was also no observable change in the ocular pigmentation of control mice versus treated mice, over the time period studied (data not shown).

TABLE 1

Plasma Tyrosine Concentrations in Control and NTBC treated (4 mg/kg q.o.d) $Tyr^{c-2J/c-2J}$ and $Tyr^{c-h/c-h}$ Mice After 30 Days of Treatment

| Group | $Tyr^{c-2J/c-2J}$ (OCA1a model) | $Tyr^{c-h}$ (OCA1b model) |
|---|---|---|
| Control | 109 ± 30 µM (n = 6) | 74 ± 25 µM (n = 6) |
| NTBC Treatment | 673 ± 73 µM (n = 4, $p = 1 \times 10^{-7}$) | 305 ± 35 µM (n = 4, $p = 2 \times 10^{-6}$) |

Example 2

This example demonstrates the effect of clinically-relevant doses of NTBC in a mouse model of oculocutaneous albinism, type OCA1b, (C57BL/6J-$Tyr^{c-h/c-h}$, carrying a temperature-sensitive mutation in tyrosinase) using predefined ocular, systemic and biochemical outcome variables.

The Himalayan mouse line is a mutant C57BL/6 mouse line which carries a temperature sensitive allele of tyrosinase, $Tyr^{c-h}$ (MGI Accession ID #72456), that spontaneously arose in a C57BL/6 mouse in 1958, and has since been inbred into the C57BL/6 background. The maximum activity of the tyrosinase produced from this allele occurs at temperatures below normal body temperature (37° C.), because the mutant protein (c.A1259G, p.H420R) is heat labile. In homozygotes, the first coat is a uniform light tan. At the first molt, the body hair becomes lighter and the ears, nose, tail, and scrotum become dark as in Siamese cats. The eyes are slightly pigmented and appear red. Himalayan mice were housed in standard conditions, at room temperature. Because the Himalayan allele retains some residual enzymatic activity, it is thought that these mice are a suitable model for type OCA1b oculocutaneous albinism.

Using the same protocol as described above, baseline plasma tyrosine, coat color (gross and microscopic), anterior segment pigment, and posterior segment pigment was documented for each mouse prior to initiating experiments. At least ten C57BL/6J-$Tyr^{c-h/c-h}$ mice, age 3-4 months, were treated with about 25 µg NTBC in a volume of about 0.2-0.3 ml, every other day, via oral gavage for a four-week period. These treated mice were compared to an age- and gender-matched cohort of C57BL/6J-$Tyr^{c-h/c-h}$ mice over the same time period. Corneal irritation due to NTBC treatment was monitored daily. At the start of treatment, an area of hair was plucked/shaved from each mouse's back, which has the effect of stimulating new hair growth and possibly new pigment deposition in the hair shaft. At the end of four weeks' time, plasma tyrosine concentrations were assessed in both treated and control animals.

Assessment of the effect treatment and the end of the experimental time period commences with photodocumentation of coat color, anterior segment pigment and posterior segment pigment of each mouse. The mice were sacrificed using standard $CO_2$ euthanasia protocol. One eye from each mouse was submitted for light microscopy, while the other is prepared for electron microscopy. Liver and kidney tissues were collected and processed for light microscopy histology, to insure no pathology is associated with treatment. Additional blood samples were taken and frozen at the time of euthanasia, for possible future studies. Hair shafts in plucked and non-plucked areas were examined and photographed under light microscopy. Melanosome number and size was quantified in the retinal pigmented epithelial cells (RPE) and choroid of the posterior pole of both treated and untreated mice, in a masked fashion, as previously described above.

Results. As in Example 1 above, eight $Tyr^{c-h/c-h}$ mice were treated and plasma tyrosine levels were ascertained after one month. At this dose, over this interval, no phenotypic changes were noted and plasma tyrosine concentrations were not statistically significantly different between treated and control animals.

The dosing of NTBC in eight $Tyr^{c-h/c-h}$ mice was increased to 4 mg/kg orally, every other day. Plasma tyrosine measurements of control and treated animals are presented in Table 1. NTBC treatment resulted in approximately a 4-fold increase in steady-state plasma tyrosine concentrations in $Tyr^{c-h/c-h}$ mice (data not shown).

It was found that biochemical changes were accompanied by phenotypic changes in the $Tyr^{c-h/c-h}$, but not the $Tyr^{c-2J/c-2J}$ mice. New pigment was deposited in hair shafts of the mice as they grew. To stimulate this growth, a patch of hair on the back of control and treated animals was shaved immediately prior to randomization. Photographs of the anterior and posterior segment ocular pigmentation were also taken before and after the study period. While the coat and ocular pigmentation of $Tyr^{c-2J/c-2J}$ mice were grossly unchanged over the one month period, there was a observable increase in pigmentation in the treated $Tyr^{c-h/c-h}$ mice compared to control $Tyr^{c-h/c-h}$ mice. In some cases, pigmentation extended beyond the immediate area that was shaved and other areas that were previously somewhat pigmented (e.g., the nose) (data not shown).

Figure 3:
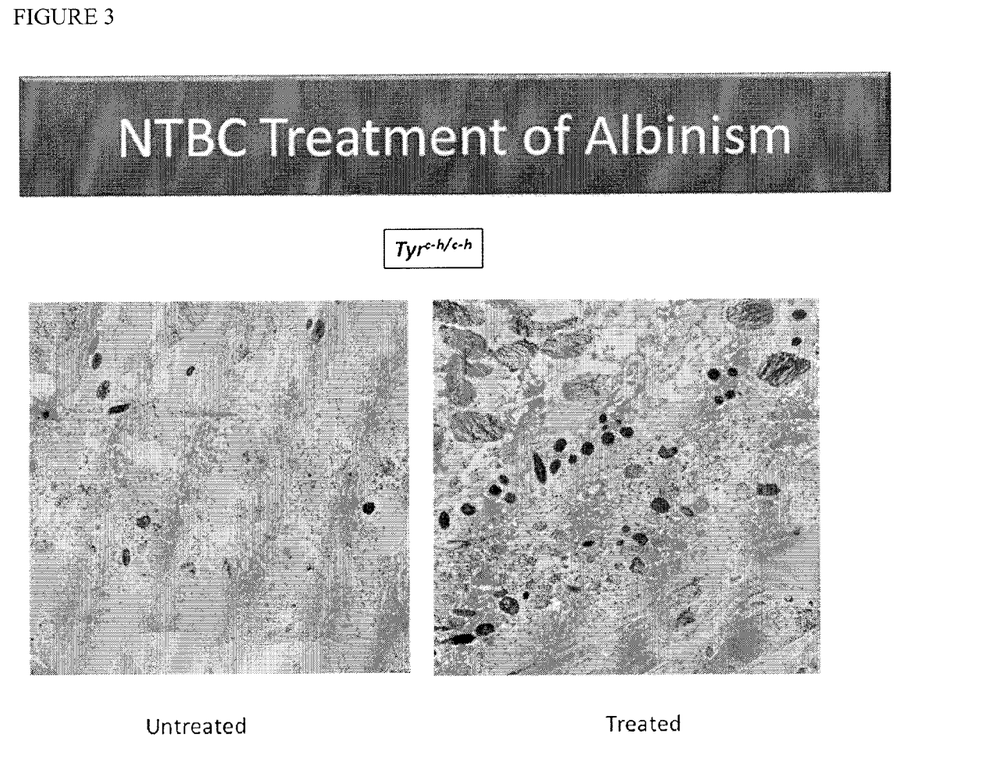
FIG. 3 shows a comparison of electron micrographs of retinal pigment epithelial (RPE) cells from C57BL/6J-Tyr$^{c-h/c-h}$ mice, which are a model for oculocutaneous albinism. The micrographs show increases in melanosomes (dark circles) in the mice treated with NTBC when compared to controls.

While the irides of the Himalayan mice in the control group and pre-treatment showed a near complete absence of pigmentation, all animals in the treated group showed some increase in iris pigmentation (data not shown). Fundus pigmenation was also grossly unchanged. However, when examined at the level of electron microscopy, preliminary data showed an significant increase in the RPE and choroidal melanosome pigment content in treated, but not control mice (FIG. 3).

Example 3

In this example, a pediatric patient study for treatment of vision problems associated with oculocutaneous albinism type OCA1b is provided.

Patient recruitment begins with genotype testing to determine which type of albinism each clinical subject. Patients are screened based on the gene that is mutated, for example, tyrosinase (OCA1), the P protein gene (OCA2), the tyrosinase-related protein-1 (TYRP-1, OCA3), and the MATP gene (OCA4). OCA1-the most common form of OCA in North American Caucasians, can be further divided into those individuals who lack tyrosinase activity (OCA1a) and those who have some residual tyrosinase activity (OCA1b). Clinical molecular testing of the tyrosinase gene is used to identify mutations in patients who meet the clinical criteria for albinism, but who make some pigment. The effect of the mutation on enzymatic activity is determined experimentally.

Vision assessment of all patients is undertaken to measure visual acuity, contrast sensitivity (with and without glare), reading speed, pigment production (via photography), nystagmus, strabismus and photophobia, using standard methods in the art.

The patients are then randomized and assigned to blinded control and treatment groups. The treatment groups are further divided into two dosage levels: 0.7 mg/kg/day and 1.0 mg/kg/day. The length of the study is ninety days. Each week during the study, and at the end of the thirty day trial, visual assessments of the patients are taken. In addition, observations of any other clinical manifestations of increased pigmentation are noted. At the end of the study the visual measurements of the patients in the two treatment arms are compared with those of the control arm and significant statistical differences between the groups are discerned.

Example 4

This example provides evidence that treatment with NTBC increases melanin content in the melanosomes of ocular tissues.

Figure 4:
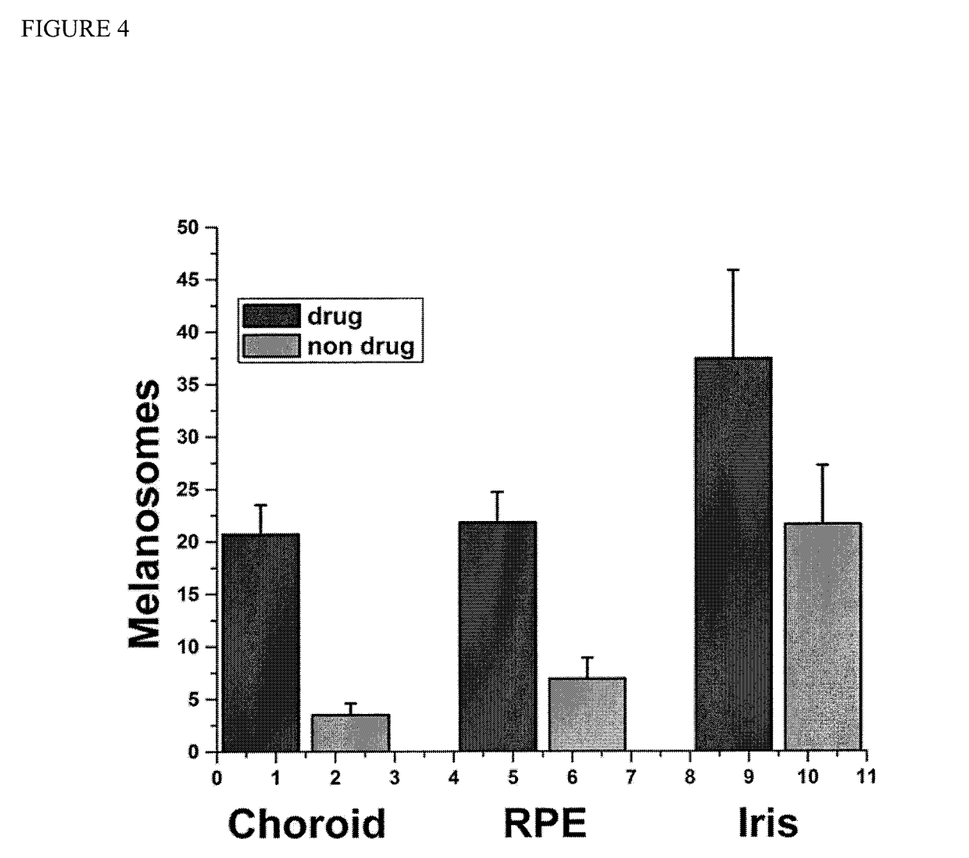
FIG. 4 is a comparison of the number of pigmented melanosomes in ocular tissues of vehicle- and NTBC-treated C57BL/6-Tyr$^{c-h/c-h}$ (Himalayan) mice.

In order to quantitate the effect of NTBC on pigmentation in ocular tissues and to assess for sub-clinical changes in ocular pigmentation, transmission electron microscopy (TEM) of iris, retinal pigment epithelium (RPE), and choroid of treated and control mice (n=4 eyes from 2 mice for each group) was performed. When TEM images of iris, choroid and RPE of NTBC-treated $Tyr^{c-2J/c-2J}$ mice were compared with those of untreated mice, little to no increase in the number of pigmented melanosomes (stages III and IV) was observed, consistent with our clinical observations (data not shown). The small amount of pigment present in treated mice was irregular and not clearly in melanosomes. In contrast, TEM images of iris, choroid, and RPE of NTBC-treated $Tyr^{c-h/c-h}$ mice showed a clear increase in the number of pigmented melanosomes when compared with controls. This difference was statistically significant in all three tissues examined (FIG. 4).

Example 5

The following example describes how prenatal treatment with NTBC increases coat and iris pigmentation in Tyr$^{c-h/c-h}$ pups.

In order to assess whether elevation of plasma tyrosine by NTBC treatment could have an effect early in development, pregnant Tyr$^{c-h/c-h}$ females were treated with 4 mg/kg NTBC. While pups of vehicle-treated mothers had coat color similar to wild-type, the pups of NTBC-treated mothers were considerably darker. Ocular examinations performed near the time of weaning showed that irides of pups born to vehicle-treated mothers resembled that of untreated Himalayan mice. The irides of pups born from NTBC-treated mothers, however, showed significant pigmentation on clinical examination. There was no significant difference between the fundus appearance of pups born to vehicle-treated and drug-treated dams (data not shown). The pups of treated mothers had no obvious congenital malformations or systemic illnesses. These data suggest that NTBC's effectiveness in increasing ocular and cutaneous pigmentation in Himalayan mice extends into the prenatal/neonatal period.

Example 6

In the following example, in silico modeling of mouse tyrosinase mutations agrees with in vivo observations.

It was thought that NTBC exerted its pigment-increasing effect in Himalayan mice by increasing tyrosine concentrations, which, in turn, acts as a molecular chaperone for tyrosinase. In order to explain the differing effects of NTBC on the two OCA models studied, the predicted effect of the c-2J (R77L) and c-h (H420R) tyrosinase mutants were modeled in silico.

The minimization procedure and molecular dynamics (MD) simulations were performed with the Impact module of the Maestro program package (version 8.0.308, Schrodinger, Inc., New York, N.Y., USA). Hydrogen atoms were added to the structure of mouse tyrosinase and the structure was regularized by an energy minimization procedure using the OPLS_2005 potentials, the 12 Å non-bonded cut-offs, the distance-dependent dielectric constant and 100 steepest descent steps of minimization followed by 200 steps of conjugated gradient in the presence of 7135 SPC water molecules on the final step. MD trajectories were calculated in a periodic rectangular box of explicit SPC water molecules. The structures of the enzyme and EGF-like domains were equilibrated using the SPC water box with dimensions 70 Å×70 Å×70 Å for the tyrosinase enzyme domain and EGF-like motif. All bonds were constrained by the linear constraint solver algorithm. The temperature was kept constant to 298.15 K. Isotropic pressure coupling of the system and fast particle-mesh Ewald electrostatics were applied. Solvent was equilibrated by 20 ps of solute positions restrained MD (20 000 of 1 fs steps). Finally, the quality of the predicted structure was tested with the program Procheck (R. A. Laskowski, et al., *J. Appl. Cryst.*, 26:283 (1993)).

Because X-ray crystallography has not been successfully performed on mammalian tyrosinase, the homology-modeling analyses previously-reported and presented here rely, in part, on the available crystal structures of prokaryotic (*Streptomyces Castaneoglobisporus*) and mushroom tyrosinase, invertebrate hemocyanin, and plant catechol oxidase (see, J.

C. Garcia-Borron, et al., *Pigment Cell Res.*, 15:162 (2002); W. P. Gaykema, et al., *J. Mol. Biol.*, 187:255 (1986); T. Klabunde, et al., *Nat. Struct. Biol.*, 5:1084 (1998); T. Schweikardt et al., *Pigment Cell Res.*, 20:394 (Oct, 2007); M. Sendovski, et al., *J. Mol. Biol.*, 405:227 (2011); Y. Matoba, et al., *J. Biol. Chem.*, 281:8981 (2006)).

The c-2J mutation, R77L, occurs in a structural fragment at the amino terminus that is identified by the Simple Modular Architecture Research Tool (SMART) (http://smart.embl-heidelberg.de/) as an EGF/laminin-like domain. While the precise function of this domain is not known, the R77L mutation is predicted to have major structural consequences based on the negative blosum70 score (−3) and significant Grantham distance of 102. Structure equilibration using 3ps molecular dynamics suggests that the mutational change has a dramatic effect on tyrosine binding, which is thought to occur at the hydrophobic surface of the catalytic site. As such, it was thought that elevating ambient tyrosine concentrations would have little to no effect on baseline enzyme function, in agreement with in vivo results found.

In contrast, the Himalayan (c-h) mutation, H420R, demonstrates a blosum70 score of 0 and a smaller Grantham distance of 29, both of which suggest a less severe structural change. Rather than directly affecting the structure of the hydrophobic tyrosine binding pocket, the model described herein predicts a greater effect on the coordination of copper near the active site. As such, these results are consistent with in vivo data described herein.

Example 7

This example describes how elevated tyrosine concentrations stabilize H420R, but not R77L, tyrosinase.

Figure 5:
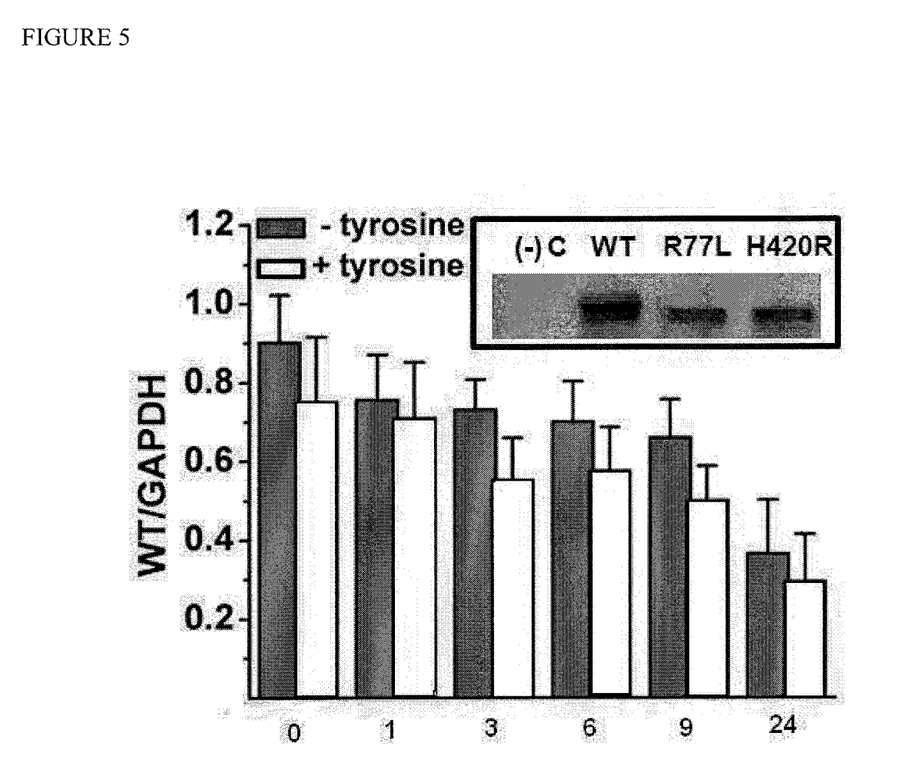
FIG. 5 is a graph showing the steady state levels of wild-type tyrosinase, stabilized relative to GAPDH at various time points by 1 mM tyrosine.
Figure 6:
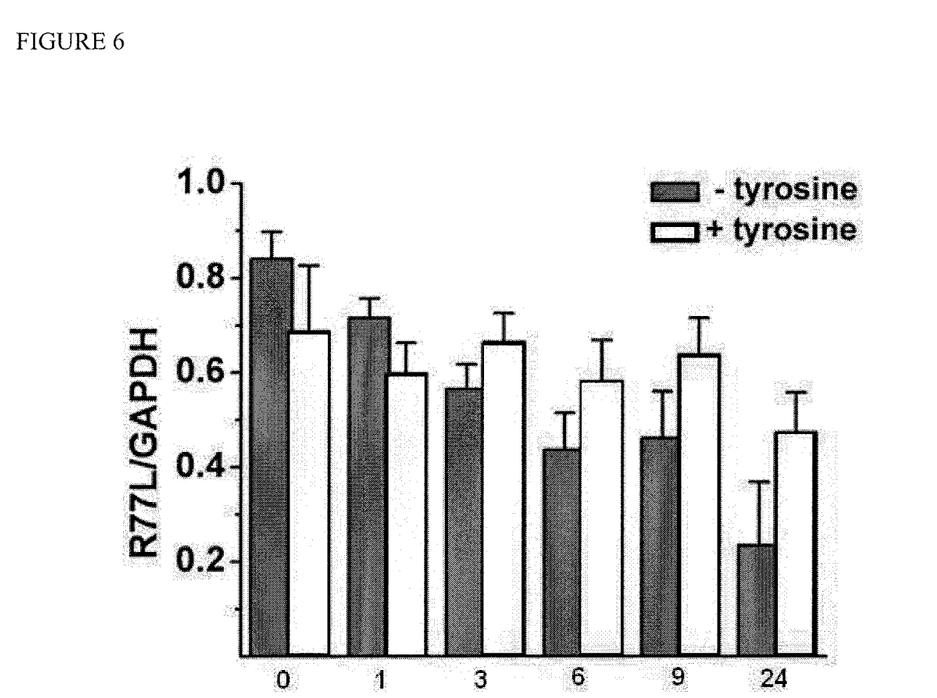
FIG. 6 is a graph showing the steady state levels of R77L tyrosinase, stabilized relative to GAPDH at various time points by 1 mM tyrosine.
Figure 7:
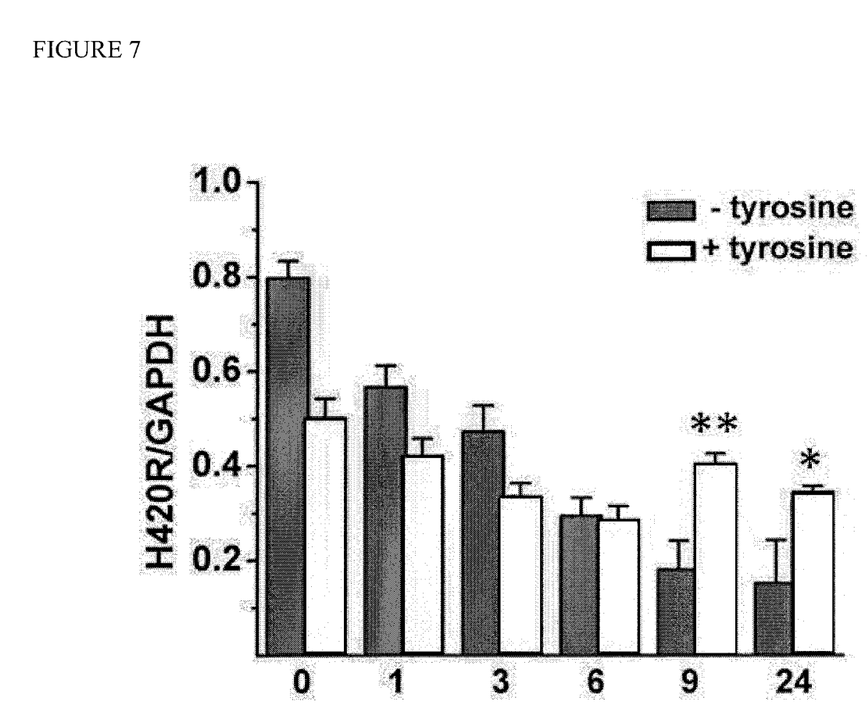
FIG. 7 is a graph showing the steady state levels of H420R tyrosinase, stabilized relative to GAPDH at various time points by 1 mM tyrosine. The stability of the H420R—but not the R77L—protein is stabilized relative to GAPDH at later time points (9 and 12 hours) by 1 mM tyrosine. Two-tailed test of significance: p-value<0.0001 (**), p-value<0.05 (*).

Given the in silico analysis described above, it was hypothesized that H420R but not R77L tyrosinase can effectively bind tyrosine, and that elevated ambient tyrosine could act as a molecular chaperone and selectively stabilize the Himalayan protein. In order to test this hypothesis, either wild-type, R77L, or H420R mutant tyrosinase proteins were expressed in Chinese-hamster ovary (CHO) cells, and tyrosinase protein stability was measured using cycloheximide to inhibit new protein synthesis. Similar levels of wild-type and mutant protein expression were observed on Western blots of cell protein lysates at baseline (FIG. 5). As predicted, 1 mM tyrosine improved the stability of the H420R mutant protein (FIG. 6) at later time points (9 and 24 hours) relative to a marker protein, GAPDH. Although there was a trend towards stabilization of the R77L mutant with 1 mM tyrosine, this was not statistically significant (FIG. 7). These results agree with the in vivo observations that pharmacological elevation of plasma tyrosine increases pigmentation in the Himalayan model of OCA-1B, but not in the Tyr$^{c-2J/c-2J}$ model of OCA-1A.

Example 8

In this example, elevated tyrosine concentrations result in pigment production in melanocytes expressing OCA-1B, but not OCA-1A, Tyr alleles in vitro.

Figure 8:
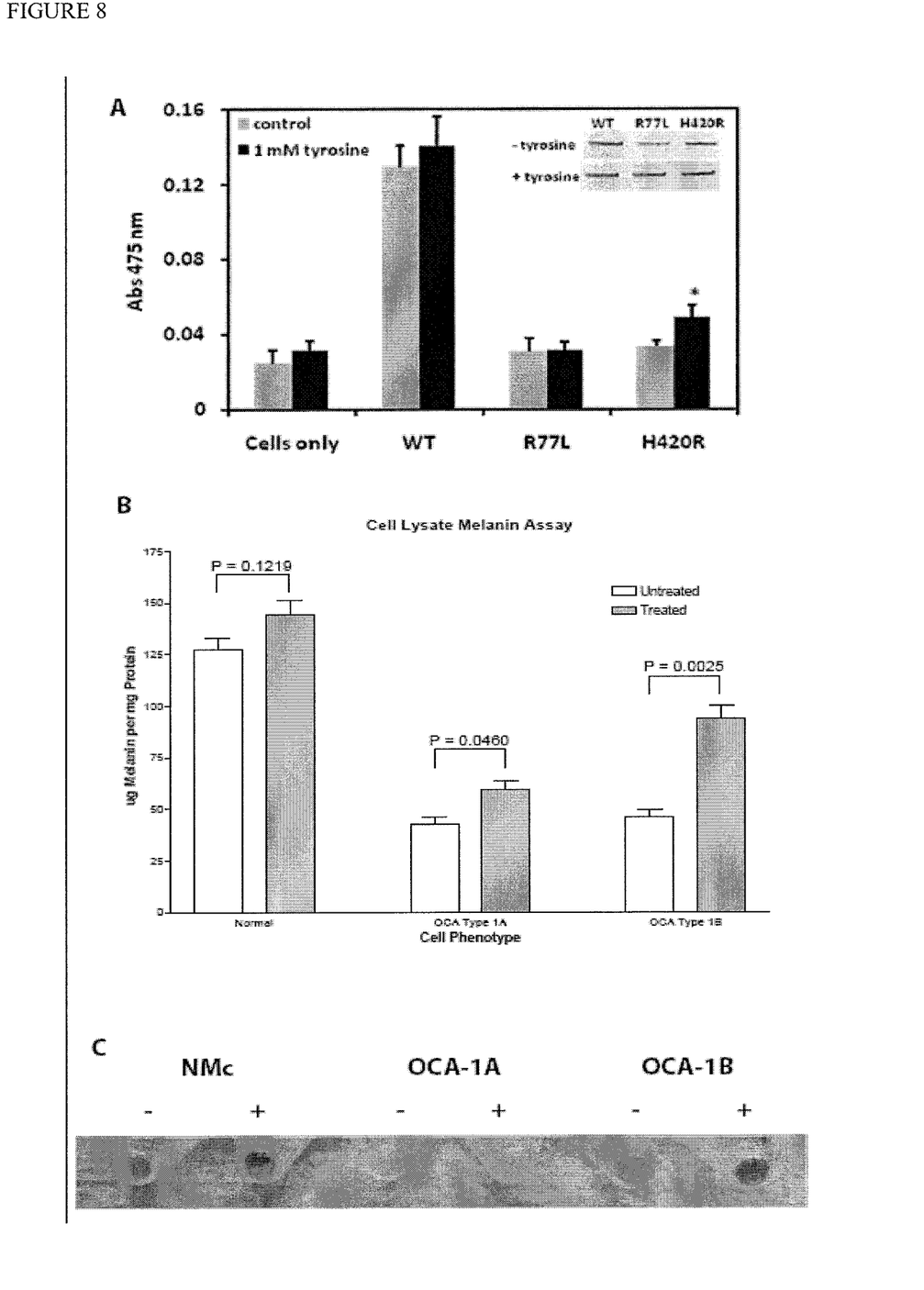
FIG. 8 shows that increased ambient tyrosine promotes pigment production in OCA-1B, but no OCA-1A, allele-expressing cells. (8A) Although Melan-c cells transfected with WT, R77L, or H420R tyrosinase express comparable levels of protein (inset), only the H420R tyrosinase responds to 1 mM tyrosine by increasing pigment production. (8B, 8C) Cultured human melanocytes from control and OCA1-B, but not OCA-1A patients show increased pigment on incubation with 1 mM tyrosine.

The ability of R77L and H420R mutant proteins to produce pigment in vitro, compared to wild-type protein, in albino mouse melanocytes (Melan-c cells, D. C. Bennett et al., *Development* 105:379 (1989)) was also investigated. Mirroring our in vivo results, 1 mM tyrosine increased enzyme activity over baseline in Melan-c cells expressing the H420R mutant tyrosinase (p=0.03), but not R77L mutant tyrosinase (FIG. 8A).

In addition, the response of human melanocytes cultured from the skin of OCA-1A and OCA-1B patients was studied. Similar to our results with transfected mouse Melan-c cells, wild-type melanocytes produce significant melanin in the presence of 1 mM tyrosine (FIGS. 8B, 8C). Melanocytes from an OCA-1A patient did not produce detectable pigment either in the presence or absence of 1 mM tyrosine. Melanocytes from a patient with OCA-1B showed baseline amounts of pigment similar to untreated controls. However, treatment with 1 mM tyrosine significantly increased pigmentation (p=0.0025), albeit not to the level observed in wild-type melanocytes. These in vitro results suggest that elevation of circulating tyrosine can increase pigmentation in humans with residual tyrosinase activity, implying that the effect observed in Himalayan mice may generalizable to other hypomorphic alleles of TYR/Tyr, and supports the idea that administration of an effective amount of NTBC to humans can provide at least a temporary increase in the pigmentation of the skin for cosmetic uses.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of treating impaired vision in a subject suffering from oculocutaneous albinism or ocular albinism, the method comprising administering to the subject a pharmaceutical composition comprising (a) 2-(-2-nitro-4 trifluoromethylbenzoyl)-1,3cyclohexanedione (NTBC) or a pharmaceutically acceptable salt, hydrate, or solvate thereof, and (b) a pharmaceutically and physiologically acceptable carrier in an amount effective to increase the number of pigmented melanosomes in retinal pigment epithelium (RPE) cells and treat impaired vision in the subject suffering from oculocutaneous albinism or ocular albinism.

2. The method of claim 1, comprising increasing plasma concentrations of tyrosine from about 7 micromolar ($\mu$M) to about 2 millimolar (mM) in the subject.

3. The method of claim 1, comprising increasing plasma concentrations of tyrosine from about 50 $\mu$M to about 300 $\mu$M in the subject.

4. The method of claim 1, comprising increasing plasma concentrations of tyrosine of about 70 $\mu$M in the subject.

5. The method of claim 1, comprising administering NTBC to the subject in an amount between about 0.1 mg/kg/day to about 10 mg/kg/day.

6. The method of claim 1, comprising administering NTBC to the subject in an amount between about 0.5 mg/kg/day to about 4 mg/kg/day.

7. The method of claim 1, comprising administering NTBC to the subject in an amount between about 1 mg/kg/day to about 2 mg/kg/day.

8. The method of claim 1, comprising administering NTBC to the subject in an amount of about 1 mg/kg/day.

9. The method of claim 1, wherein the oculocutaneous albinism is type OCA1a oculocutaneous albinism.

10. The method of claim 1, wherein the oculocutaneous albinism is type OCA1b oculocutaneous albinism.

11. The method of claim 1, wherein the albinism is type 1 ocular albinism.

12. The method of claim 1, wherein the albinism is due to a mutation in the tyrosinase gene, the GPR143 gene, the P protein gene (OCA2), the tyrosinase-related protein-1 (TYRP-1, OCA3) gene, and/or the microtubulin associated protein tau (MATP, OCA4) gene.

13. The method of claim 1, comprising increasing visually discernible pigmentation in the eyes, hair or skin for cosmetic purposes.

14. The method of claim 1, comprising increasing pigmentation in the iris or the choroid of the eyes of the subject.

15. The method of claim 1, comprising increasing the number of pigmented melanosomes in the iris or choroid of the eyes of the subject.

* * * * *